United States Patent [19]

Eisenberg

[11] 4,024,643

[45] May 24, 1977

[54] DENTAL MATRIX RETAINER

[76] Inventor: Harry H. Eisenberg, 201 W. Springfield, Champaign, Ill. 61820

[22] Filed: Aug. 25, 1975

[21] Appl. No.: 607,287

[52] U.S. Cl. .................................................. 32/63
[51] Int. Cl.² .......................................... A61C 5/12
[58] Field of Search ......................................... 32/63

[56] References Cited

UNITED STATES PATENTS

| 278,674 | 5/1883 | Wiesbauer | 32/63 X |
| 2,674,801 | 4/1954 | Trangmar | 32/63 |

Primary Examiner—Robert Peshock
Attorney, Agent, or Firm—Coffee & Sweeney

[57] ABSTRACT

A dental matrix retainer in the form of a longitudinally split band having separate band portions for looping about the axially inner or gingival contour of a tooth and about the axially outer or cusp contour of the tooth. The two adjacent band portions have opposed notches in alignment along adjacent edges thereof for cooperating to define a singular aperture through which filling material may protrude into contact with an adjacent tooth, whereby the two band portions can be transversely separated and removed longitudinally from between the teeth after a cavity is filled without disturbing the contact.

13 Claims, 6 Drawing Figures

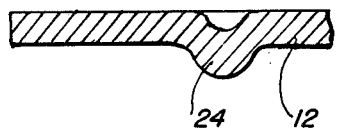
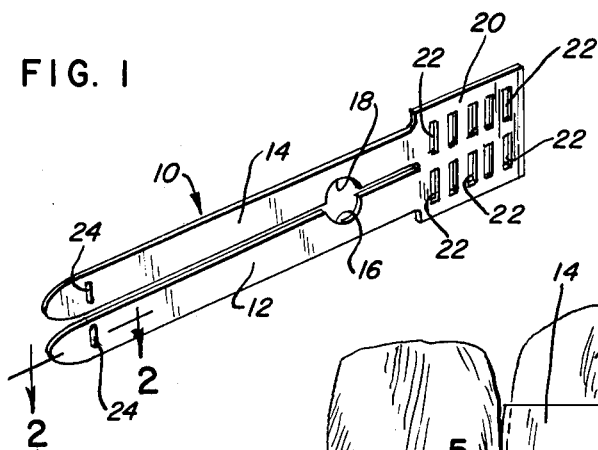
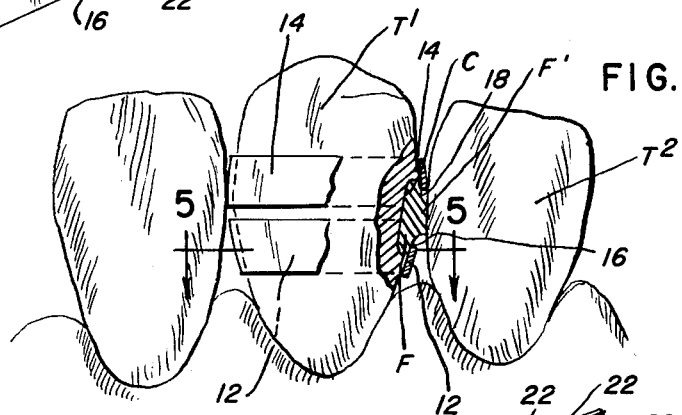
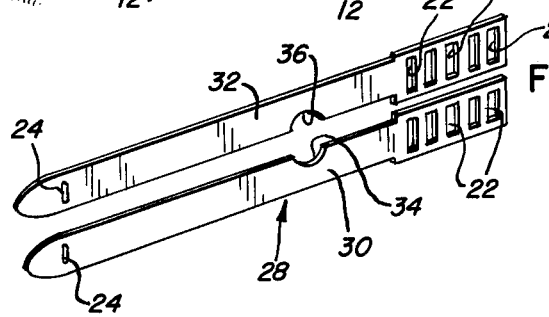
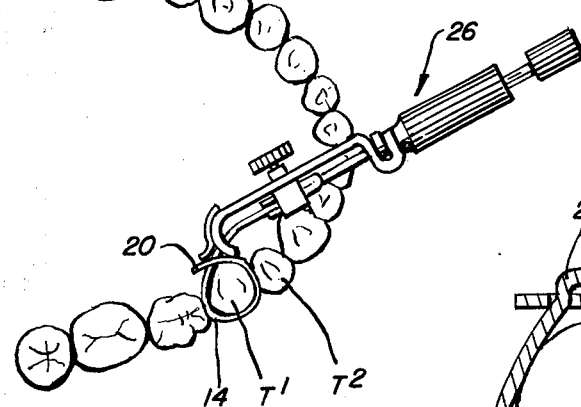
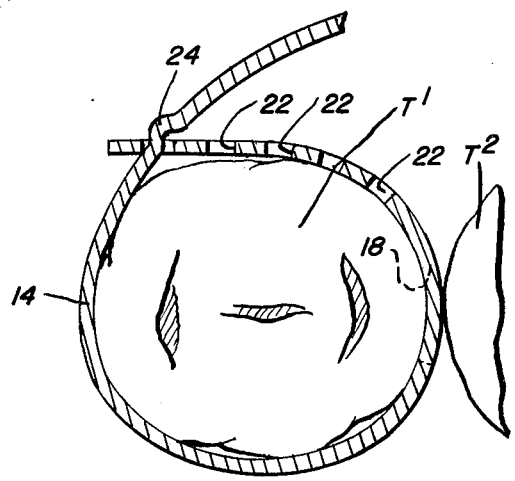

DENTAL MATRIX RETAINER

BACKGROUND AND SUMMARY OF THE INVENTION

This invention relates to an improved dental matrix retainer and, particularly, a novel retainer for use in filling a cavity whereby the filling material protrudes beyond the cavity into contact with an adjacent tooth.

Dental matrix bands or retainers have been known and utilized for a considerable period for time for looping around an axial contour of a tooth which is to be restored. The band is fashioned with an aperture through which is filling material may be inserted into a cavity on the side of the banded tooth. The band is maintained in snug embracing relation with the axial contour of the tooth during the restoration in order to shape the filling by forming a temporary wall for the filling mateiral.

However, it has been found in many circumstances that it is desirable for the filling material to protrude beyond the cavity into contact with an adjacent tooth to prevent further diseases and discomfort caused by many restorations. With the prior known dental matrix retainers, with the central apertures, it is impossible to remove the matrix band without disturbing the contact point between the teeth or the restoraton. This invetion is directed to solving this probelem by providing a new and improved dental matrix retainer.

Accordingly, an object of the present invention is to provide a dental matrix retainer of the character described which is in the form of a split band having a pair of elongated adjacent band portions which are wrapped about a tooth adjacent parallel relationship. The band portions have a pair of opposed notches, one formed in the adjacent edge of each band portion for cooperating with the notch of the other band portion to define a singular aperture through which filling material may protrude into contct with an adjacent tooth. In this manner, after the cavity has been filled and the tooth restored the two band portions can be transversely separated and removed longitudinally from between the teeth without disturbing the contact point or the restoration.

In one form of the invention, the split band portions are separate individual bands having the notches cut out of the edges thereof whereby the bands may be looped about the axially inner or gingival contour of a tooth and the axially outer or cusp contour of the tooth with the notches in opposed alignment to form the aperture.

In another form of the invention, the matrix retainer is unitary with the two elongated adjacent band portions formed form a single sheet of thin material for looping about a tooth. The band portions are integral at adjacent ends and separated at opposite ends, with the opposed notches aligned in adjacent inner edges of the band portions to define the singular aperture.

In either form of the invention, means is provided to removably maintain the bands or band portions snugly about the contours of the respective portions of the tooth to be restored. The maintaining means comprises longitudinal series of transverse slots at one end of the bands are in the interconnected portions of the unitary band. The opposite ends of the bands or band portions are sufficiently narrow for positioning in a selected one of the slots and a raised detent is engageable within the slot to maintain the bands or band portions snugly about a tooth. Of course, the slots and detents can be eliminated and a standard clamping block used to maintain the bands about a tooth.

Other objects, features and advantages of the invention will be apparent from the following detailed description taken in connection with the accompanying drawings.

DESCRIPTION OF THE DRAWINGS

FIG. 1 is a perspective view of one form of the dental matrix retainer of the present invention;

FIG. 2 is a partial horizontal section, on an enlarged scale, taken generally along line 2—2 of FIG. 1;

FIG. 3 is an elevational view showing the matrix retainer in position about a tooth with a cavity restoration completed and having a contact with an adjacent tooth;

FIG. 4 is a plan view showing a standard clamping block for use with the matrix retainer of the present invention;

FIG. 5 is a sectional view, on an enlarged scale, through one of the band portions showing the slot and detent type maintaining means; and FIG. 6 is a perspective view, similar to that of FIG. 1, or another form of the invention.

DETAILED DESCRIPTION OF THE INVENTION

Referring to the drawings in greater detail, and first to FIG. 1, one form of dental matrix retainer, generally designated 10, in accordance with the present invention is shown in perspective. The retainer is a "split retainer" having a first thin band portion 12 for looping about the axially inner or gingival contour of a tooth (see FIG. 3) and a second thin band portion 14 for looping about the axially outer or cusp contour of the tooth (also see FIG. 3) for restoring a tooth $T^1$ by filling a cavity C with filling material F so that the filling material has a contact portion F' which maintains a contact point with an adjacent tooth $T^2$.

The first or lower (as viewed in FIG. 3) band portion 12 has a notch 16 formed in the edge thereof facing the upper or cusp portion of the tooth, and the the band portion 14 has a complementary notch 18 opposite the notch 16 to define a single aperture through which the filling material may protrude as shown in FIG. 3 and described above into contact with tooth $T^2$.

In the form of the invention shown in FIG. 1, the matrix retainer is unitary and formed form a single sheet of thin material, such as metal, with the band portions 12 and 14 interconnected at adjacent ends by an enlarged sheet portion 20. As seen in FIG. 1, the opposite ends of the band portions 12 and 14 are separated.

Means is provided to removably maintain the band portions 12 and 14 snugly about the contour of the tooth $T^1$ during the restoration of the tooth. More particularly, two longitudinal series of transverse slots 22 are provided in the interconnecting portion of 20 of the retainer. As can be seen in FIG. 1, the band portions 12 and 14 are narrowed so as to be of a width for receipt within the slots 22 and are provided with raised detents 24 (see FIGS. 2 and 5) for engagement with one of the slos 22 to maintain the band portions snugly about the tooth. The plural slots accommodate different diameter teeth.

Thus, with the embodiment of the invention shown in FIG. 1, after the tooth $T^1$ has been restored by filling the cavity C with filling material F and with the filling material maintaining a contact point F' with tooth T², the split matrix retainer 10 can be removed by transversely separating the band portions 12 and 14 and then longitudinally pulling the band portions from between the teeth after the detents 24 have been moved out of the slots 22, without disturbing the contact material F' or the restoration.

Of course, a standard clamping block, generally designated 26 in FIG. 4, may be utilized with the slotted retainer. An example of such a clamping block is shown in U.S. Pat. No. 2,591,745.

Another form of matrix retainer, generally designated 28, is shown in FIG. 6 and comprises two cooperating but separate band portions 30 and 32 having complementary cooperating notches 34 and 36, respectively, to form a singular aperture for restoring the tooth T¹. As with the embodiment of the invention shown in FIG. 1, slots 22 ae provided for receiving the opposite ends of the bands 30 and 32, with detents 24 engageable in the slots 22 to maintain the separate bands in position about a tooth.

As with the form of the invention shown in FIG. 1, the separate bands 30 and 32 form a temporary wall for the filling material in order to shape the material, while permitting a contact point with the adjacent tooth. After the first tooth is restored, the separate bands can be removed individually from between the teeth without disturbing the contact point therebetween or the new restoration.

The foregoing detailed description has been given for clearness of understanding only and no unnecessary limitations should be understood therefrom as some modifications will be obvious to those skilled in the art.

I claim:

1. A dental matrix retainer, comprising:
   a first thin band for looping about the axially inner or gingival contour of a tooth, said first band having a notch formed in the edge thereof facing the outer or cusp portion of the tooth; and
   a second thin band for looping about the axially outer or cusp contour of the tooth said second band having a complementary cooperative notch formed in the edge thereof facing the inner or gingival portion of the tooth and complementing and cooperating with the notch in said first band when the two bands are adjacent each other to define a unitary matrix with said notches forming a singular aperture through which filling material may protrude into contact with an adjacent tooth, whereby the two bands can be removed longitudinally from between said teeth after a cavity is filled without disturbing said contact.

2. The dental matrix retainer of claim 1 including means to removably maintain said bands snugly about the contours of the respective portions of the tooth.

3. The dental matrix retainer of claim 2 wherein said maintaining means comprises a longitudinal series of transverse slots at one end of each band, the opposite ends of the bands being sufficiently narrow for receipt in any selected one of said slots and having detent means engageable within a slot to maintain the bands snugly about the tooth.

4. The dental matrix retainer of claim 1 wherein said bands are defined by adjacent parallel band portions of a unitary retainer, the band portions being interconnected at adjacent ends and separated at opposite adjacent ends, with said notches being disposed in opposed alignment along the adjacent edges of the band portions.

5. The dental matrix retainer of claim 4 wherein said unitary retainer is formed from a single thin sheet of material.

6. The dental matrix retainer of claim 4 including means to removably maintain said unitary retainer snugly about the contour of the tooth.

7. The dental matrix retainer of claim 6 wherein said maintaining means comprising a pair of longitudinal series of transverse slots at the band interconnected end thereof, said band portions being sufficiently narrow at the opposite ends thereof for receipt in a selected one of said slots and having detent means engageable within a slot to maintain the band portions snugly about the tooth.

8. A unitary dental mataix retainer, comprising: a pair of elongaged adjacent band portions formed form a single sheet of thin material for looping about a tooth, the band portions being integral at adjacent ends and separated at opposite adjacent ends, means for removably maintaining the adjacent badn portions about the contour of a tooth, and a pair of opposed notches one formed in the adjacent edge of each band portion for cooperating to difine a singular aperture through which filling mataeral may protrude into contact with an adjacent tooth, whereby the two band portions ca be transversely separated and removed longitudinally from between said teeth after a cavity is filled without disturbing said contact.

9. The dental matrix retainer of cliam 8 wherein said maintaining means comprises a pair of longitudinal series of transverse slots at the band interconnected end thereof, said band portions being sufficiently narrow at the opposite ends thereof for receipt in a selected one of said slots and having detent means engageable withih a slot to maintain the band portions snugly about the tooth.

10. A dental matrix retainer, comprising:
   a first thin band for looping about the axially inner or gingival contour of a tooth, said first band having a notch formed in the edge thereof facing the outer or cusp portion of the tooth; and
   a second thin band for looping about the axially outer or cusp contour of the tooth said second band having a notch formed in the edge thereof facing the inner or gingival portion of the tooth and cooperating with the notch in said first band when the two bands are adjacent each other to define a singular aperture through which filling material may protrude into contact with an adjacent tooth, whereby the two bands can be removed longitudinally form between said teeth after a cavity is filled without disturbing said contact, said bands being defined by adjacent parallel and portions of a unitary retainer, the band portions being interconnected at adjacent ends and separated at opposite adjacent ends, with said notches being disposed in opposed alignment along the adjacent edges of the band portions.

11. The dental matrix retainer of claim 10 wherein said unitary retainer is formed from a single thin sheet of material.

12. The dental matrix retainer of claim 10 including means to removably maintain said unitary retainer snugly about the contour of the tooth.

13. The dental matirx retainer of claim 12 wherein said maintaining means comprises a pair of longitudinal series of transverse slots at the band interconnected end thereof, said band portions being sufficiently narrow at the opposite ends thereof for receipt in a selected one of said slots and having means engageable within a slot to maintain the band portions snugly about the tooth.

* * * * *